United States Patent
Lee et al.

(10) Patent No.: US 7,118,551 B1
(45) Date of Patent: Oct. 10, 2006

(54) NON-METAL REINFORCING MANDREL

(75) Inventors: Jeong S. Lee, Diamond Bar, CA (US); Ken Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/470,009

(22) Filed: Dec. 22, 1999

(51) Int. Cl.
*A61M 29/00* (2006.01)

(52) U.S. Cl. .................................. 604/96.01

(58) Field of Classification Search ........... 604/164.01, 604/164.13, 264, 96.01, 93.01, 95.03, 164.1, 604/164.11, 528, 523, 524, 525
See application file for complete search history.

(56) References Cited

U.S. PATENT DOCUMENTS

| | | | |
|---|---|---|---|
| 4,536,533 A * | 8/1985 | Chen et al. | 524/161 |
| 4,762,129 A | 8/1988 | Bonzel | |
| 4,775,371 A | 10/1988 | Mueller, Jr. | |
| 4,950,257 A * | 8/1990 | Hibbs et al. | 604/265 |
| 5,147,317 A * | 9/1992 | Shank et al. | 604/164 |
| 5,176,637 A | 1/1993 | Sagae | |
| 5,195,971 A | 3/1993 | Sirhan | |
| 5,226,880 A | 7/1993 | Martin | |
| 5,242,396 A * | 9/1993 | Evard | 604/96 |
| 5,246,420 A * | 9/1993 | Kraus et al. | 604/95 |
| 5,294,395 A * | 3/1994 | Broyer | 264/178 F |
| 5,300,025 A | 4/1994 | Wantink | |
| 5,334,148 A | 8/1994 | Martin | |
| 5,376,084 A | 12/1994 | Bacich et al. | |
| 5,418,308 A * | 5/1995 | Harvie | 526/336 |
| 5,425,711 A | 6/1995 | Ressemann et al. | |
| 5,454,795 A | 10/1995 | Samson | |
| 5,470,315 A | 11/1995 | Adams | |
| 5,496,294 A | 3/1996 | Hergenrother et al. | |
| 5,507,768 A | 4/1996 | Lau et al. | |
| 5,520,645 A * | 5/1996 | Imran et al. | 604/95 |
| 5,531,690 A | 7/1996 | Solar | |
| 5,545,134 A | 8/1996 | Hilaire et al. | |
| 5,545,138 A | 8/1996 | Fugoso et al. | |
| 5,549,552 A | 8/1996 | Peters et al. | |
| 5,549,556 A | 8/1996 | Ndondo-Lay et al. | |
| 5,599,326 A | 2/1997 | Carter | |
| 5,611,775 A | 3/1997 | Machold et al. | |
| 5,649,909 A | 7/1997 | Cornelius | |
| 5,658,264 A | 8/1997 | Samson | |
| 5,720,724 A | 2/1998 | Ressemann et al. | |
| 5,782,740 A | 7/1998 | Schneiderman | |
| 5,782,811 A | 7/1998 | Samson et al. | |
| 5,795,341 A | 8/1998 | Samson | |
| 5,810,867 A | 9/1998 | Zarbatany et al. | |
| 5,827,242 A | 10/1998 | Follmer et al. | |
| 5,836,892 A * | 11/1998 | Lorenzo | 600/585 |
| 5,853,400 A | 12/1998 | Samson | |
| 5,868,706 A | 2/1999 | Cox | |

(Continued)

FOREIGN PATENT DOCUMENTS

EP  0277368  12/1987

(Continued)

*Primary Examiner*—Nicholas D. Lucchesi
*Assistant Examiner*—Christopher D. Koharski
(74) *Attorney, Agent, or Firm*—Fulwider Patton LLP

(57) ABSTRACT

An apparatus for providing support along the length of a catheter is described. The present invention consists of a mandrel fabricated from a non-metal. The mandrel extends through the lumen of a dilatation catheter to provide added support and stiffness to the catheter shaft. The stiffness along the length of the non-metal mandrel may easily be varied by making dimensional or morphological changes to the polymeric mandrel.

15 Claims, 1 Drawing Sheet

U.S. PATENT DOCUMENTS

| | | |
|---|---|---|
| 5,876,386 A | 3/1999 | Samson |
| 5,891,112 A | 4/1999 | Samson |
| 5,895,378 A * | 4/1999 | Nita .......................... 604/529 |
| 5,897,911 A | 4/1999 | Loeffler |
| 6,004,279 A * | 12/1999 | Crowley et al. ............ 600/585 |
| 6,004,291 A | 12/1999 | Ressemann et al. |
| 6,179,810 B1 * | 1/2001 | Wantink et al. .......... 604/96.01 |
| 6,224,535 B1 * | 5/2001 | Chiu et al. ..................... 600/3 |
| 6,599,288 B1 * | 7/2003 | Maguire et al. ............... 606/27 |
| 6,733,486 B1 * | 5/2004 | Lee et al. ................... 604/525 |

FOREIGN PATENT DOCUMENTS

| | | |
|---|---|---|
| EP | 0515119 A1 | 5/1992 |
| WO | WO 90/08567 | 1/1990 |
| WO | WO 93/18813 | 3/1993 |
| WO | 95/16862 | 12/1995 |

\* cited by examiner

NON-METAL REINFORCING MANDREL

BACKGROUND OF THE INVENTION

1. Field of the Invention

The present invention relates generally to catheters. More particularly, the present invention relates to a non-metal reinforcing mandrel for use with such catheters.

2. Description of Related Art

In percutaneous transluminal coronary angioplasty (PTCA), catheters are inserted into the cardiovascular system via the femoral artery under local anesthesia. A preshaped guiding catheter is positioned in the coronary artery, and a dilatation catheter having a distensible balloon portion is advanced through the guiding catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery. After the last dilation, the balloon is deflated so that the dilatation catheter can be removed from the dilated stenosis and blood flow can resume through the dilated artery.

Ongoing development work of the dilatation catheters has reduced the transverse dimensions of the catheters for angioplasty procedures both as to their outer diameters as well as to the wall thickness of the catheter's tubular components. This reduction has led to difficulties in designing dilatation catheters having small transverse dimensions while still maintaining adequate pushability for advancement of the dilatation catheter through the guiding catheter into the patient's coronary artery and across tight stenoses. The marginal or inadequate pushability has been particularly noticeable with over-the-wire catheters that have been adapted for use with guidewires having diameters not more than about 0.014 inch (0.356 mm).

One solution to this dilemma has been the use of a reinforcing mandrel 24, such as the one shown in FIGS. 1A and 1B. The catheter 10 typically has an inner tubular member 12 with an inner lumen 14 adapted to receive a guidewire with a maximum OD of less than about 0.014 inch. An outer tubular member 16 is generally disposed about the inner tubular member 12 such that the inner tubular member 12 extends through the outer tubular member 16 and an outer lumen 18 is defined therebetween. The inflatable member (e.g., a balloon) 20 has a proximal end 21 which is secured to the distal end of the outer tubular member 16 and a distal end 23 secured to the distal end of the inner tubular member 12 so as to seal off the outer lumen 18 and the interior of the inflatable member 20.

The reinforcing mandrel 24 is within the outer lumen 18 between the inner 12 and outer 16 tubular members and extends from the proximal end of the catheter 10 into the distal portion of the catheter 10 but typically ends short of the inflatable member 20. The mandrel 24 is usually a cylindrical, often tapered axle inserted onto a device such as a catheter 10 to provide support along the length of the given device. The mandrel 24 is typically secured at the proximal end of the mandrel 24 within the adapter (not shown) mounted at the proximal end of the catheter 10.

Although difficult to achieve during processing, it is often desirable to vary the diameter of the mandrel 24 to establish a predetermined amount of flexibility. For example, since it is generally desirable for the proximal section of the catheter 10 to be more stiff to assist in the catheter's pushability, the proximal section of the mandrel 24 is designed/fabricated to have a larger diameter than the diameter of the mandrel 24 in a more distal section of the catheter 10. The smaller diameter portion of the mandrel 24 extending into the distal section of the catheter shaft 10 preferably has a transverse dimension of at least 20% less than the transverse dimension of the proximal section of the mandrel 24. This variation in the diameter of the mandrel 24 provides flexibility in the distal portion of the catheter 10 and allows the catheter 10 to track over the guidewire while still maintaining excellent pushability.

The mandrel 24 of the prior art is fabricated from a metal or metal alloy (hereinafter metal) rod. The metal mandrels 24 known in the prior art, however, have several inherent limitations. First, metal rods are generally too stiff for angioplasty procedures, and a too stiff rod reduces a catheter's trackability over a guidewire or other medical device. Not only is the rod often too stiff, but a metal rod is also more difficult to process. For example, the metal rod must be ground to the desired diameter for the various (i.e., proximal and/or distal) section and often still retains sharp edges along its length that can damage the interior of the catheter shaft. Further, the dimensions of a metal mandrel are fixed during fabrication.

It would be advantageous to replace the metal mandrels of the prior art with a non-metal mandrel that has more easily varied dimensions and stiffness characteristics along the length of the mandrel. The ability to easily vary the dimensions and stiffness characteristics of a mandrel will also allow more freedom in the choice of materials for the catheter shaft itself. In other words, because the stiffness of the mandrel can be easily varied during processing, the proximal section of the mandrel can be made stiff enough to provide the desired pushability for the catheter. A mandrel having a stiff proximal section reduces the need for a stiff proximal section of the catheter shaft itself. Thus, the material for the proximal shaft of the catheter will no longer be limited to a stiff polymer. By allowing the use of a less stiff polymer in the proximal section, the non-metal mandrel will also substantially reduce the likelihood of kinking. In this manner, a mandrel having a stiffer proximal section will provide the desired pushability without having to sacrifice the flexibility of the distal shaft of the catheter.

SUMMARY OF THE INVENTION

An apparatus for providing support along the length of a catheter is described. The present invention consists of a mandrel fabricated from a non-metal. The mandrel may extend through the outer lumen of a dilatation catheter to provide added support and stiffness to the catheter shaft. The stiffness along the length of the non-metal mandrel may easily be varied by making dimensional or morphological changes to the polymeric mandrel.

BRIEF DESCRIPTION OF THE DRAWINGS

The invention is further described by way example with reference to the accompanying drawings, wherein.

DETAILED DESCRIPTION OF THE INVENTION

An apparatus for providing support for a catheter is described. In the following detailed description, numerous specific details are set forth in order to provide a more thorough understanding of the present invention. However, it will be appreciated that the present invention may be practiced without these specific details. In other instances, well-known devices, methods, procedures, materials, and individual components have not been described in detail so as not to unnecessarily obscure aspects of the present invention.

A mandrel is usually a cylindrical, often tapered, axle/rod inserted into a device such as a catheter to provide support along the length of the device. In the prior art, mandrels used with biomedical devices have been fabricated from a metal or metal alloy (hereinafter metal). The metal mandrels, however, have been encumbered by several limitations including difficulty in processing mandrels having a desired varying diameter, sharp edges that may damage the device the mandrel is inserted into, and an often excessive stiffness. The present invention addresses each of the above issues by providing a non-metal mandrel.

Figure 1A:
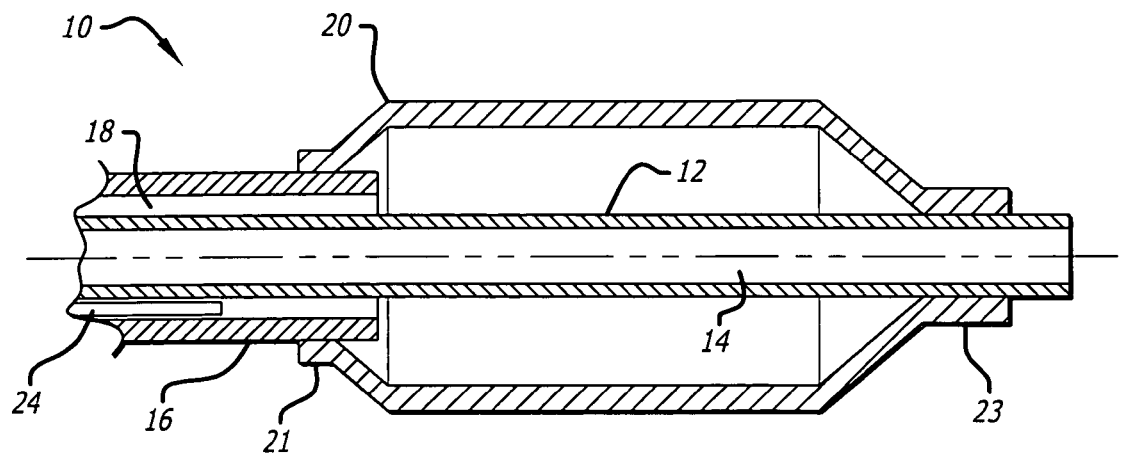
FIG. 1A is a side cross-sectional view of a mandrel of a first embodiment of the present invention as used with a dilation catheter.
Figure 1B:
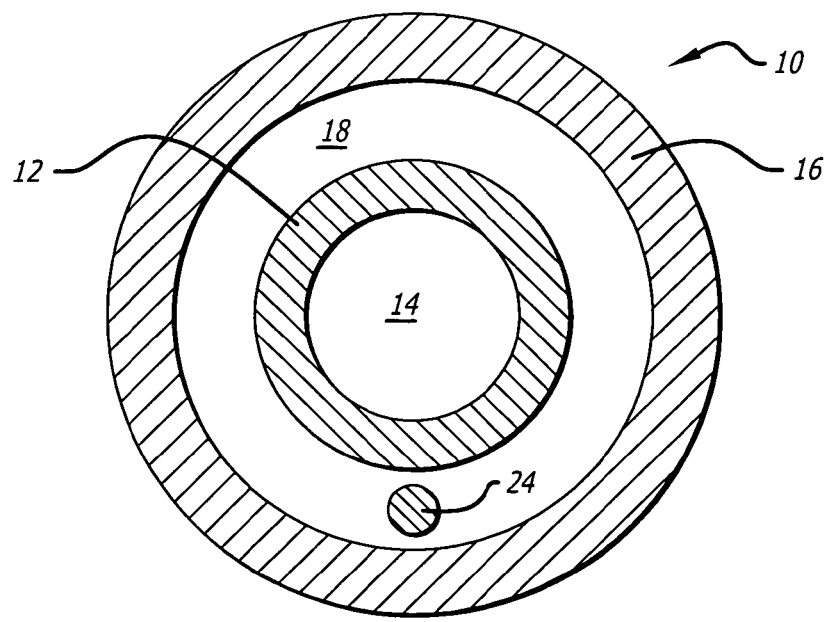
FIG. 1B is a front cross-sectional view of the mandrel and catheter illustrated in FIG. 1A.

FIGS. 1A and 1B are illustrations of a reinforcing mandrel 24 used with a dilatation catheter 10. The catheter 10 has an inner tubular member 12 with an inner lumen 14 adapted to receive a guidewire (not shown). An outer tubular member 16 is generally disposed about the inner tubular member 12 such that the inner tubular member 12 extends through the outer tubular member 16 and an outer lumen 18 is defined therebetween. The inflatable member (e.g., a balloon) 20 has a proximal end 21 that is secured to the distal end of the outer tubular member 16, and a distal end 23 that is secured to the distal end of the inner tubular member 12 so as to seal off the outer lumen 18 and the interior of the inflatable member 20.

The reinforcing mandrel 24 is typically within the outer lumen 18 between the inner 12 and the outer 16 tubular members and extends from the proximal end of the catheter 10 into the distal portion/section of the catheter 10. The mandrel 24 typically ends short of the inflatable member 20.

The mandrel of the present invention is fabricated from a non-metal material. The material for the non-metal mandrel may be selected from numerous materials including, but not limited to: nylons, including high stiffness polyamides; stiff polymers with tensile modules greater than approximately 400,000 psi, such as PEEK (polyether etherketone), PPS (polyphenylene sulfide), PEI (polyetheramide), and PI (polyimide); liquid crystalline polymers; polymers reinforced with glass fibers; polymers reinforced with graphite fibers, etc.

By fabricating the mandrel of a catheter from a non-metal material, the present invention provides numerous advantages over the prior art. Without the use of a mandrel, the proximal section of a catheter shaft must generally be made of a stiff polymer in order to provide a sufficient amount of pushability. However, a stiff polymer shaft kinks easily during manipulation of the catheter into the desired position with the cardiovascular system of the patient. The metal mandrel of the prior art provides stiffness for the catheter in addition to the catheter shaft itself. However, the flexibility of a metal mandrel is difficult to vary, often resulting in a too stiff mandrel which makes the steering of the catheter much more difficult. The stiffness of the non-metal mandrel of the present invention may be varied as needed along the length of the mandrel as requested by the desired stiffness characteristics of a given section of the mandrel. For example, it is generally desirable for the proximal section of the catheter to be more stiff than the distal section of the catheter and thus the same is true for the mandrel.

Whereas with the prior art metal mandrel, grounding is one of the few means for tapering the diameter (i.e., having a diameter that gets smaller as the length of the mandrel is traversed from the proximal end to the distal end) and achieving a varying stiffness (the larger the diameter the more stiff the mandrel), non-metal mandrels may have dimensional and morphological changes achieved in a variety of ways. For example, the diameter of a non-metal mandrel may be tapered from the proximal end to the distal end, by a taper extruding, or by necking the mandrel at high temperatures during the initial fabrication of the mandrel. Sometimes, annealing the proximal portion of the mandrel induces a higher crystallinity which also makes the annealed proximal portion of the mandrel more stiff than the non-annealed distal portion of the mandrel.

By providing means for supporting a catheter shaft such that the stiffness of the support maybe varied as needed, the non-metal mandrel of the present invention also eliminates the previous limitation requiring the catheter shaft to be made of a stiff polymer in order to provide the desired pushability. Further, the non-metal mandrel of the present invention is fabricated from a material that is more compatible with the standard materials used for the catheter shaft. This compatibility between the mandrel and the catheter shaft allows the mandrel to be able to be fused to the shaft by heating if desired. The fusion process locks the mandrel in place and makes the external force and support to be applied more efficiently.

Thus, the non-metal mandrel of the present invention provides numerous advantages over the prior art metal mandrel. The non-metal mandrel allows for both dimensional and morphological changes that may be varied to control the stiffness characteristics of both the mandrel and the catheter shaft or sheath the mandrel is inserted into. The capability of varying the stiffness of the mandrel along its length allows the mandrel to provide the greater desired pushability without sacrificing the needed flexibility in the distal shaft. This also reduces the need for stiff polymer catheter shafts, which greatly reduces the chance of kinking along the catheter shaft.

What is claimed is:

1. A catheter comprising:
   an elongated catheter shaft having an inner tubular member with a lumen, and an outer tubular member disposed about the inner tubular member such that a lumen of the outer tubular member is defined therebetween; and
   a variable stiffness mandrel disposed in said outer tubular member lumen, having a solid core comprised of a non-metal material, a bonded proximal end section which fixedly secures the mandrel relative to the catheter shaft, an annealed proximal section which is located between and spaced apart from an outer surface of the inner tubular member and an inner surface of the outer tubular member and which has a first crystallinity, and a non-annealed distal section with a second crystallinity lower than said proximal section first crystallinity such that the proximal section is stiffer than the distal section.

2. The catheter of claim 1 wherein said material is selected from the group consisting of polyamides, polyetheretherketone, polyphenylene sulfide, polyetheramide, polyimide, and any combination thereof.

3. The catheter of claim 1 wherein said proximal section is larger than a diameter of said distal section of said mandrel.

4. The catheter of claim 1 further comprising an inflatable member secured to the catheter shaft, wherein said distal section of said mandrel extends to a location along the length of the catheter located in the inflatable member.

5. The catheter of claim 1 further comprising an inflatable member secured to the catheter shaft, and wherein the distal section of the mandrel extends to a location proximal to the inflatable member.

6. The catheter of claim 1 wherein said mandrel is formed by necking at high temperatures such that said proximal section is stiffer than said distal section.

7. The catheter of claim 1 wherein said mandrel is formed by taper extruding such that said proximal section is stiffer than said distal section.

8. A catheter comprising:
an outer member;
a hollow inner member extending through said outer member;
an outer lumen between said inner and outer members; and
a non-metal mandrel formed of a polyetheretherketone polymeric material, extending through said outer lumen, said mandrel having an annealed proximal section located between and spaced apart from an outer surface of the inner member and an inner surface of the outer member having a first crystallinity, and a non-annealed distal section having a second crystallinity lower than the proximal section first crystallinity, and being uniformly tapered from the proximal section to the distal section.

9. The catheter of claim 8 wherein a diameter of said proximal section is larger than a diameter of said distal section of said uniformly tapered mandrel.

10. The catheter of claim 8 further comprising an inflatable member having an inflatable interior, and comprising a proximal portion secured to a distal portion of the outer member and a distal portion secured to a distal portion of the inner member, wherein said distal section of said mandrel extends to a location along the length of the catheter located in the inflatable member.

11. The catheter of claim 8 further including an inflatable member secured to the outer member and the hollow inner member with an interior in fluid communication with the outer lumen and wherein the distal section of the mandrel extends to a location proximal to the inflatable member.

12. The catheter of claim 8 wherein said mandrel is formed by necking at high temperatures such that said proximal section is stiffer than said distal section.

13. The catheter of claim 8 wherein said mandrel is formed by taper extruding such that said proximal section is stiffer than said distal section.

14. The catheter of claim 8, wherein said mandrel is fixed to lock said mandrel in place relative to said catheter outer member.

15. The catheter of claim 8 wherein said hollow inner member defines a guidewire receiving lumen.

* * * * *